(12) United States Patent
Malinowski

(10) Patent No.: US 10,512,565 B2
(45) Date of Patent: Dec. 24, 2019

(54) SCLERAL MARKER FOR SURGICAL PROCEDURES

(71) Applicant: Susan M. Malinowski, Birmingham, MI (US)

(72) Inventor: Susan M. Malinowski, Birmingham, MI (US)

( * ) Notice: Subject to any disclaimer, the term of this patent is extended or adjusted under 35 U.S.C. 154(b) by 0 days.

(21) Appl. No.: 15/801,342

(22) Filed: Nov. 2, 2017

(65) Prior Publication Data

US 2019/0125585 A1    May 2, 2019

(51) Int. Cl.
| | |
|---|---|
| *A61B 3/10* | (2006.01) |
| *A61F 9/013* | (2006.01) |
| *A61B 90/00* | (2016.01) |
| *A61B 17/34* | (2006.01) |
| *A61B 3/16* | (2006.01) |
| *A61F 9/007* | (2006.01) |

(52) U.S. Cl.
CPC ........ *A61F 9/0136* (2013.01); *A61B 17/3417* (2013.01); *A61B 90/39* (2016.02); *A61B 3/16* (2013.01); *A61F 9/00736* (2013.01)

(58) Field of Classification Search
CPC .... A61F 2/147; A61F 9/00736; A61F 9/0136; A61F 9/00781
USPC ........ 351/200, 205, 206, 209–212, 221, 222
See application file for complete search history.

(56) References Cited

U.S. PATENT DOCUMENTS

| | | | |
|---|---|---|---|
| 6,629,980 B1 * | 10/2003 | Eibschitz-Tsimhoni | ..................... A61F 9/00754 606/107 |
| 2009/0043322 A1 * | 2/2009 | Melki | ................... A61F 9/0136 606/166 |
| 2015/0201974 A1 * | 7/2015 | DeRidder | .......... A61B 17/7074 606/102 |

\* cited by examiner

*Primary Examiner* — Brandi N Thomas
(74) *Attorney, Agent, or Firm* — Dinsmore & Shohl LLP; Cesare Sclafani

(57) ABSTRACT

A surgical instrument for marking spots at locations on the scleral limbal surface of a human eye. The instrument includes an elongated handle dimension to be handheld. A first elongated pointer extends substantially axially outwardly from one end of the handle. This pointer has a pointed free end which, when pressed against the scleral limbal surface, creates a depression in the scleral surface having a first area. A second elongated pointer also extends substantially axially outwardly from the end of the handle. The second pointer has a blunt free end which, when pressed against the scleral limbal surface, creates a depression in the scleral surface having a second area which is several times in magnitude the area of the first area.

6 Claims, 2 Drawing Sheets

SCLERAL MARKER FOR SURGICAL PROCEDURES

BACKGROUND OF THE INVENTION

I. Field of the Invention

The present invention relates generally to medical instruments and, more particularly, to a scleral marker for use in ophthalmic procedures.

II. Description of Related Art

In many ophthalmic procedures it is essential to locate the point of injection into the scleral limbal tissue at a precise location in order to ensure safety not only of the eye lens but also the PARS Plana region. For a human adult eye, the safe PARS Plana region lies at about 3.5 mm from the outer edge of the iris. Such a position essentially ensures not only safety of the retina, but also protects the lens from damage.

In order to facilitate the correct position in the scleral before the injection, there have been previously known devices known as "Melki" markers. This previously known Melki marker include an elongated handle dimensioned to be held in the hand of the surgeon. A pair of pointers extend outwardly from one end of the handle in the free ends of these two pointers are separated from each other by the desired distance, e.g. 3.5 mm.

In use, a Melki marker is pressed against the eye and moved for a short distance along the outside of the iris thus causing a depression in the sclera. It has been found that insertion of a needle through the depressed area, necessary for many medical procedures, is essentially painless to the patient.

In practice, however, it is difficult for even skilled ophthalmic surgeons to constantly accurately inject the needle into the depression caused by the Melki marker. When this happen; the patient feel a pain sensation in the eye. In Opthamology, however, the avoidance of pain for the patient is paramount.

SUMMARY OF THE PRESENT INVENTION

The present invention provides a surgical instrument for marking spots at locations on the scleral limbal surface of the human eye which avoids the previous known disadvantages of the Melki marker.

In brief, the surgical instrument of the present invention comprises an elongated handle preferably having a bend of about 150° at a point along its length. The handle may be constructed of any suitable material, such as stainless steel.

A first elongated pointer extends substantially axially outwardly from one end of the handle. This pointer has a dull pointed free end which, when pressed against the scleral limbal surface, creates a depression, but not an incision, in the scleral surface having a first area. This first area amounts to a little more than a point on the eye.

A second elongated pointer also extends substantially axially outwardly from the end of the handle, and is positioned about 3.5 mm from the first elongated pointer at their free ends. The second pointer, however, unlike the first pointer, has the blunt free end which, when pressed against the scleral libral surface, creates a depression in the scleral surface. The surface, furthermore, has a second area which is several times the area of the depression of the first pointer. As such, the second pointer creates a relatively large depression, when pressed against the eye, e.g. about 1 mm. Such a relatively large mark in the eye is relatively simple for the doctor to hit when injecting into the eye.

BRIEF DESCRIPTION OF THE DRAWING

A better understanding of the present invention will be had upon reference to the following detailed description when read in conjunction with the accompany drawing, wherein like reference numerals refer to like parts throughout the several views, and in which.

DETAILED DESCRIPTION OF A PREFERRED EMBODIMENT OF THE PRESENT INVENTION

Figure 1:
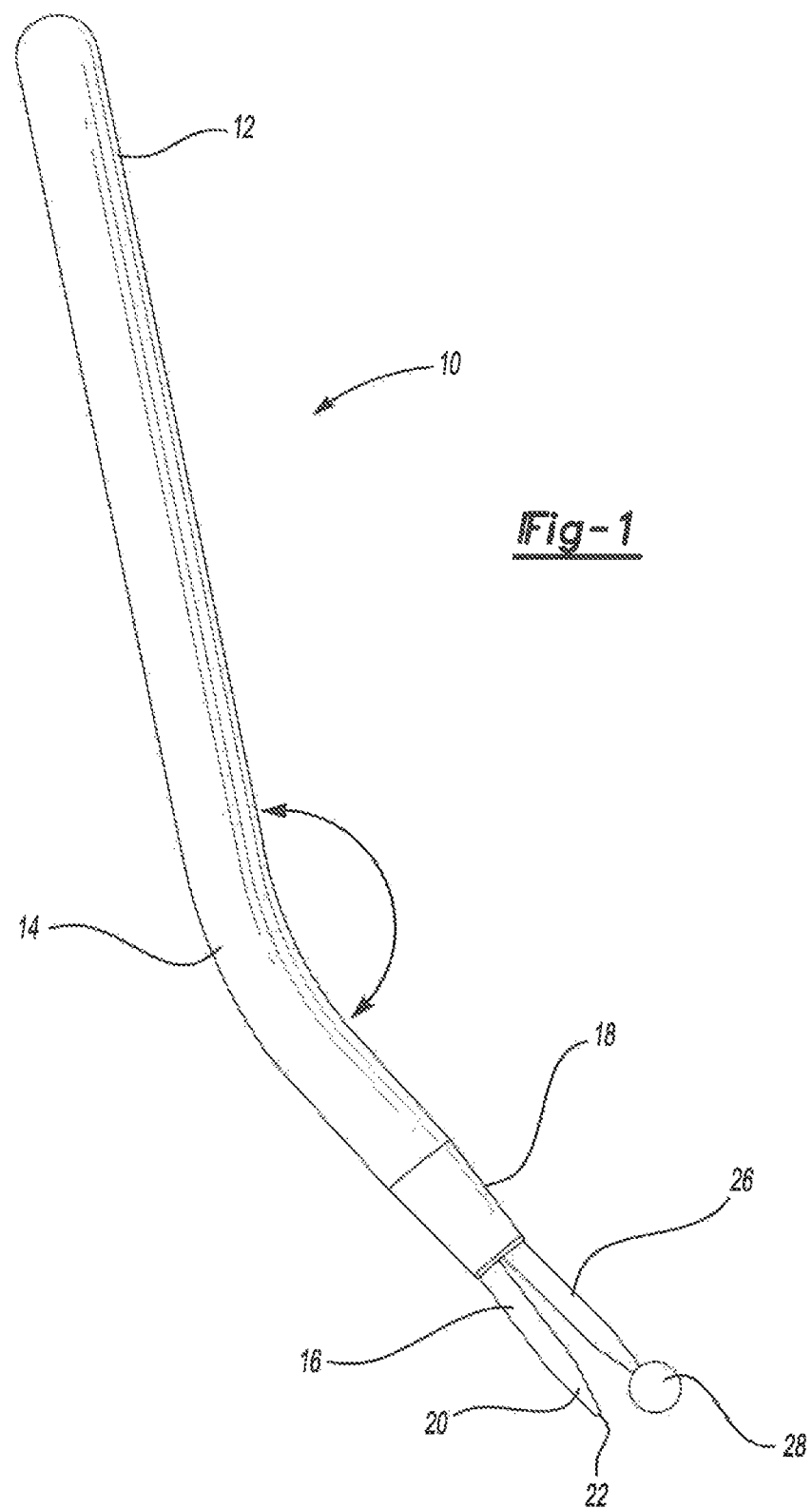
FIG. 1 is a plan view illustrating a preferred embodiment of the invention.

With reference first to FIG. 1, a preferred embodiment of the surgical instrument 10 according to the present invention is illustrated. The surgical instrument 10, as will become shortly apparent, is used for marking the human eye in preparation for eye surgery and/or injections into the human eye.

The instrument 10 includes an elongated handle 12 which is dimension to comfortably fit within the hand of the eye surgeon. The handle 12 is elongated and typically 80-100 mm in length. The handle 12 also includes a bend 14 at an intermediate point along its length and this bend is typically about 150°.

The handle 12 may be constructed of any simple material, such as stainless steel. Other materials, however, maybe used without deviation from either the spirit or scope of the invention.

A first elongated pointer 16 is secured to and extends generally axially outwardly from one end 18 of the handle 12. A free end 20 of the pointer 16 is generally conical shaped so that a pointed free end 22 of the pointer 16 has a small area of contact, i.e. less than ½ mm square in size. Furthermore, pressing the pointed free end 22 of the pointer 16 against the human eye will not puncture the scleral limbal surface 32.

A second pointer 26 also extends substantially axially outwardly from the one end 18 of the handle 12. Unlike the first pointer 16, however, the second pointer 26 terminates in a blunt free end 28 which is preferably circular in shape. Furthermore, the blunt free end 28 is dimension so that, when the blunt free end 28 of the second pointer 28 and the pointed free end 22 of the first pointer 16 of the instrument 10 press against the eye, an area of contact between the blunt free end 28 and the human eye is several times an area of contact between the pointed free end 22 and the human eye.

The pointed free end 22 of the first pointer 16 and the blunt free end 28 of the second pointer 26 are spaced apart from each other by a distance that is preferably 2 mm or less. Thus, the pointed free end 28 can be safely positioned outside the lens and in front of the retina of a human.

Figure 2:
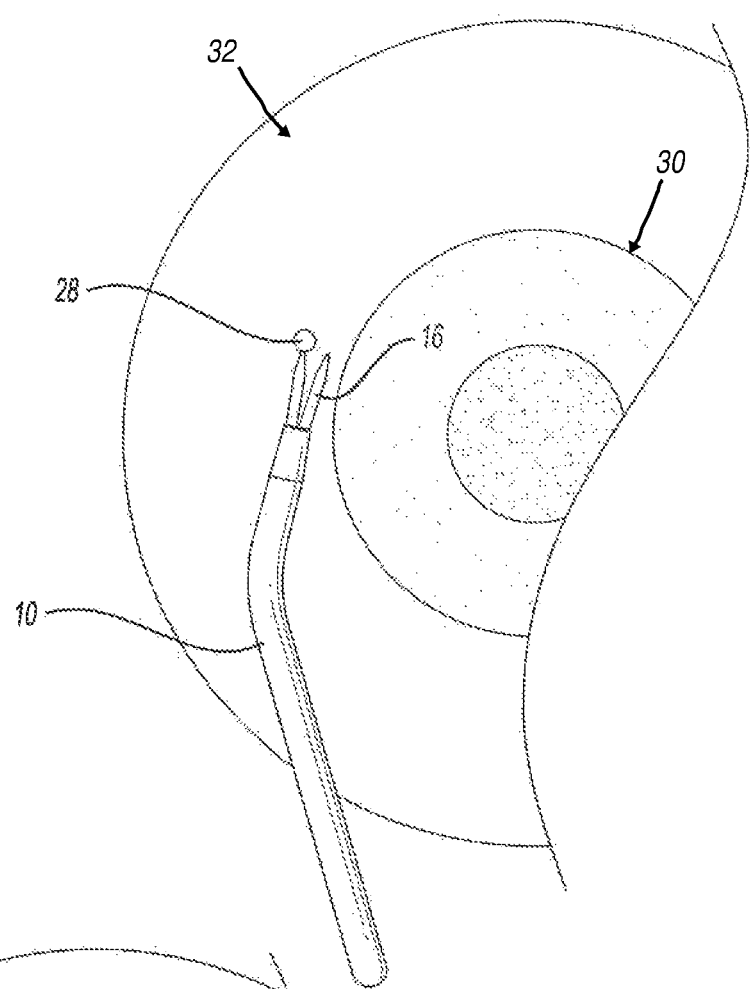
FIG. 2 is a plan view illustrating the use of the preferred embodiment of the invention.

With reference now to FIG. 2, in use the surgeon positions the pointed free end 22 of the first pointer 16 closely adjacent the outer periphery of the iris 30. A surgeon then presses the blunt free end 28 against the scleral limbal surface 32 for a relatively short time period, eg 8 seconds. The instrument 10 is then removed.

Figure 3:
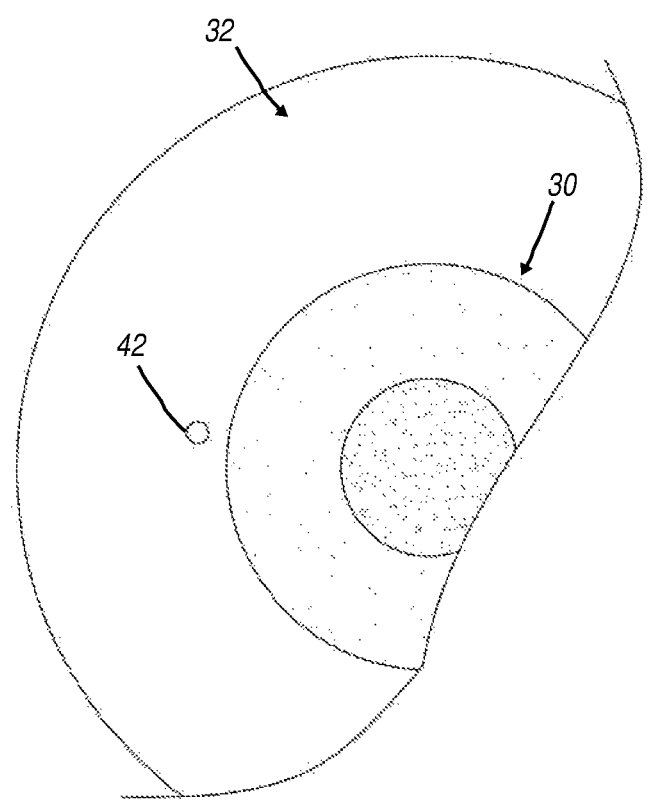
FIG. 3 is a plan view illustrating a portion of the eye following application of the surgical instrument of the present invention.

With reference now to FIG. 3, upon removal of the instrument 10 from the eye, an indentation 42 is formed in the scleral limbal surface 32 approximately midway between the outer periphery of the iris 30 and the plana mars of the eye. Furthermore, the large size of the depression made by the blunt free end 22 of the instrument 10 is not only easy for the surgeon to locate, but also facilitates injections through the depression formed by the blunt free end 28 of the second pointer 26. This, in turn, increases the patients comfort during the subsequent injection.

Even though the blunt free end 28 of the of the second pointer 26 of the instrument 10 creates a slight depression in the scleral limbal surface 32 of the eye, the depression is only temporary. After a short time, the scleral limbal surface 32 returns to its natural original shape without any known adverse effects.

From the foregoing, it can be seen in the present inventions provides a surgical instrument for ophthalmic surgery on human beings which facilitates not only the location of the PARS Plana area for injection into the eye, but also reduces pain and discomfort during the subsequent surgical operation of the injection.

Having described my invention, many modifications thereto will become apparent to those skilled in the art to which it pertains without deviation from the spirit of the invention as defined by the scope of the appended claims.

I claim:

1. A surgical instrument for marking spots at locations on the scleral limbal surface of a human eye, said surgical instrument comprising:
   an elongated handle dimensioned to be hand held,
   a first elongated pointer extending substantially axially outwardly from one end of said handle, said first elongated pointer having a pointed free end which, when pressed against the scleral limbal surface, creates a depression in the scleral limbal surface having a first area, and
   a second elongated pointer extending substantially axially outwardly from said end of said handle, said second elongated pointer having a blunt free end which, when pressed against the scleral limbal surface, creates a depression in the scleral limbal surface having a second area which is several times said first area,
   said pointed free end on said first elongated pointer being spaced from said blunt free end of said second elongated pointer.

2. The surgical instrument as defined in claim 1 wherein said blunt free end of said second elongated pointer is substantially circular in shape.

3. The surgical instrument as defined in claim 1 wherein said first elongated pointer and said second elongated pointer are each of a one piece construction.

4. The surgical instrument as defined in claim 1 wherein said pointed free end of said first elongated pointer and said blunt free end of said second elongated pointer are radially offset from each other relative to a longitudinal axis of said handle.

5. A surgical instrument for marking spots at locations on the scleral limbal surface of a human eye, said surgical instrument comprising:
   an elongated handle dimensioned to be hand held,
   a first elongated pointer extending substantially axially outwardly from one end of said handle, said first elongated pointer having a pointed free end which, when pressed against the scleral limbal surface, creates a depression in the scleral limbal surface having a first area, and
   a second elongated pointer extending substantially axially outwardly from said end of said handle, said second elongated pointer having a blunt free end, said blunt free end is substantially circular in shape which, when pressed against the scleral limbal surface, creates a depression in the scleral limbal surface having a second area which is several times said first area,
   wherein said pointed free end on said first elongated pointer being spaced apart from said blunt free end of said second elongated pointer,
   wherein said pointed free end of said first elongated pointer and said blunt free end of said second elongated pointer are radially offset from each other relative to a longitudinal axis of said handle.

6. The surgical instrument as defined in claim 5 wherein said first elongated pointer and said second elongated pointer are each of a one piece construction.

* * * * *